(12) United States Patent
Bringhen et al.

(10) Patent No.: US 12,012,570 B2
(45) Date of Patent: Jun. 18, 2024

(54) ACETATE COMPOUNDS USEFUL AS ODORANTS

(71) Applicant: Givaudan SA, Vernier (CH)

(72) Inventors: Alain Bringhen, Choulex (CH); Simon Ellwood, Hythe (GB)

(73) Assignee: Givaudan SA, Vernier (CH)

( * ) Notice: Subject to any disclaimer, the term of this patent is extended or adjusted under 35 U.S.C. 154(b) by 198 days.

(21) Appl. No.: 17/290,632

(22) PCT Filed: Nov. 14, 2018

(86) PCT No.: PCT/EP2018/081156
§ 371 (c)(1),
(2) Date: Apr. 30, 2021

(87) PCT Pub. No.: WO2020/098927
PCT Pub. Date: May 22, 2020

(65) Prior Publication Data
US 2022/0119733 A1    Apr. 21, 2022

(51) Int. Cl.
*C11B 9/00* (2006.01)
*C07C 69/14* (2006.01)

(52) U.S. Cl.
CPC ............ *C11B 9/0049* (2013.01); *C07C 69/14* (2013.01); *C07C 2602/18* (2017.05)

(58) Field of Classification Search
None
See application file for complete search history.

(56) References Cited

U.S. PATENT DOCUMENTS 3,937,723 A     2/1976  Schulte-Elte
4,318,831 A  *  3/1982  Klein ................... C07C 29/147
                                                        560/231

FOREIGN PATENT DOCUMENTS

| CN | 101528655 A | 9/2009 |
|---|---|---|
| CN | 102361844 A | 3/2010 |
| EP | 0801049 A2 | 10/1997 |
| EP | 3135663 A1 | 3/2017 |
| WO | 2008046239 A1 | 4/2008 |
| WO | 2010109391 A1 | 9/2010 |
| WO | 2011101181 A1 | 8/2011 |

OTHER PUBLICATIONS

International Search Report for Application No. PCT/EP2018/081156 dated Jul. 16, 2019.
Written Opinion of the International Searching Authority for Application No. PCT/EP2018/081156 dated Jul. 16, 2019.
Database Registry Accession No. 94231-48-8, Chemical Abstracts Service, XP002792555, Sep. 8, 1985.
Jerzy A. Bajgrowicz, et al., Synthesis and Structure Elucidation of a New Potent Sandalwood-Oil Substitute, Helvetica Chimica Acta, 1998, pp. 1349-1358, vol. 81, Issue 5-8, Wiley.
Delasalle, Celine et al. Structure-Odor Relationships of Semisynthetic b-Santalol Analogs, Chemistry & Biodiversity, vol. 11 (2014), pp. 1843-1860.
Cheng, Li Ping et al. QSAR of a-campholenic derivatives with sandalwood odor, and molecular design, Monatsh Chem., vol. 141 (2010), pp. 953-959.
Chinese Patent Office Search Report, Chinese Patent Application No. 201880099475.7 dated Nov. 2023.

* cited by examiner

*Primary Examiner* — Jessica Whiteley
(74) *Attorney, Agent, or Firm* — Curatolo Sidoti & Trillis Co., LPA; Salvatore A. Sidoti; Floyd Trillis, III

(57) ABSTRACT

The present invention refers to acetates possessing woody creamy sandalwood olfactory properties. The invention further refers to fragrance compositions and consumer products comprising them.

16 Claims, No Drawings

ACETATE COMPOUNDS USEFUL AS ODORANTS

CROSS REFERENCE TO RELATED APPLICATION

This application is a national stage application of International Application No. PCT/EP2018/081156, filed 14 Nov. 2018 of which application is incorporated herein by reference in its entirety.

The present invention relates to new odorants possessing woody creamy sandalwood olfactory properties. The invention furthermore refers to methods for their production, and to fragrance compositions containing these.

In the fragrance and flavor industry, perfumers and flavorists are continually looking for new compounds.

Surprisingly, we have now found a new class of acetates that possess woody creamy sandalwood odor profiles.

There is provided in a first embodiment a compound of formula (I)

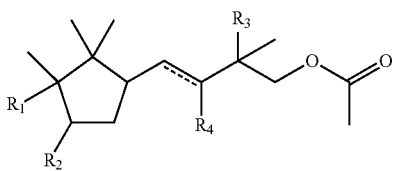

(I)

wherein $R^1$ and $R^2$ form together with the carbon atoms to which they are attached cyclopropyl or a double bond, or $R^1$ and $R^2$ are hydrogen; and $R^3$ and $R^4$ form together with the carbon atom to which they are attached cyclopropyl or a double bond, and the dotted line together with the carbon-carbon bond forms a single bond; or $R^3$ and $R^4$ are hydrogen, and the dotted line together with the carbon-carbon bond forms a double bond.

The compounds of formula (I) comprise one or more chiral centers and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

As a specific example of compounds of formula (I), one may cite, as non-limiting example, (1-methyl-2-((1,2,2-trimethylbicyclo[3.1.0]hexan-3-yl)methyl)cyclopropyl)-methyl acetate, possessing a soft, woody creamy sandalwood character with a soft fruity floral aspect (violet/orris direction). All four diastereoisomers of this compound contribute to its overall odor characteristics, but only one of the diastereomers was found to constitute the main odor vector (rel-(1S, 2S)-(1-methyl-2-(((1S,3R,5R)-1,2,2-trimethylbicyclo[3.1.0]hexan-3-yl)methyl)-cyclopropyl)methanol).

Further, non-limiting examples are compounds of formula (I) selected from (E)-2-methyl-4-(1,2,2-trimethylbicyclo[3.1.0]hexan-3-yl)but-2-en-1-yl acetate; (E)-2-methyl-4-(1,2,2-trimethylbicyclo[3.1.0]hexan-3-yl)but-3-en-1-yl acetate, (E)-2-methyl-4-(2,2,3-trimethylcyclopentyl)but-3-en-1-yl acetate; (E)-2-methyl-4-(2,2,3-trimethylcyclopentyl)but-2-en-1-yl acetate; (E)-2-methyl-4-(2,2,3-trimethylcyclopent-3-en-1-yl)but-3-en-1-yl acetate; (E)-2-methyl-4-(2,2,3-trimethylcyclopent-3-en-1-yl)but-2-en-1-yl acetate; (1-methyl-2-((2,2,3-trimethylcyclopent-3-en-1-yl)methyl)cyclopropyl)methyl acetate; and (1-methyl-2-((2,2,3-trimethylcyclopentyl)methyl)cyclopropyl)methyl acetate.

The compounds of formula (I) may be used alone, as stereoisomeric mixture, or in combination with known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art. As used herein, "carrier material" means a material which is practically neutral from a odorant point of view, i.e. a material that does not significantly alter the organoleptic properties of odorants.

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a fragrance composition. A detailed description of the nature and type of adjuvants commonly used in fragrance compositions containing same cannot be exhaustive, but it has to be mentioned that said ingredients are well known to a person skilled in the art.

As used herein, 'fragrance composition' means any composition comprising the compound of formula (I) and a base material, e.g. a diluent conventionally used in conjunction with odorants, such as diethyl phthalate (DEP), dipropylene glycol (DPG), isopropyl myristate (IPM), pentane-1,2-diol, triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

The following list comprises examples of known odorant molecules, which may be combined with the compounds of formula (I):

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11- trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl) propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane];

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3, 3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

In one particular embodiment the compounds of formula (I) may be combined with other known woody odorants, such as Javanol™ (1-methyl-2-[[(1S,3R,5R)-1,2,2-trimethylbicyclo[3.1.0]hex-3-yl]methyl]cyclopropanemethanol), Ebanol™ ((E)-3-Methyl-5-(2,2,3-trimethyl-3-cyclopenten-1-yl)-4-penten-2-ol), Radjanol™ (2-Ethyl-4-(2,2,3-trimethyl-3-cyclopenten-1-yl)-2-buten-1-ol), Polysantol™ (3,3-Dimethyl-5-(2,2,3-trimethyl-3-cyclopenten-1-yl)-4-penten-2-ol), Osyrol™ (3,7-Dimethyl-7-methoxy-2-octanol), Sandalore™ (3-Methyl-5-(2,2,3-trimethylcyclopent-3-en-1-yl)pentan-2-ol), Sandela™ (3-(5,5,6-Trimethylbicyclo[2.2.1]hept-2-yl)cyclohexan-1-ol), Polysant™ (3,3-Dimethyl-5-(2,2,3-trimethyl-3-cyclopenten-1-yl)-4-penten-2-ol), and the like to reinforce the natural woody character.

In certain embodiments the compounds of formula (I) may be combined with other woody odorants in the range from 0.05:99.95 to 99.95:0.05 (e.g. in the range from 0.5:99.5 to 5:95 (compound of formula (I) or mixture thereof: woody odorant(s)).

In one particular embodiment the compound of formula (I) is (1-methyl-2-((1,2,2-trimethylbicyclo[3.1.0]hexan-3-yl)methyl)cyclopropyl)methyl acetate and the other woody odorant is (1-methyl-2-(((1S,3R,5R)-1,2,2-trimethylbicyclo[3.1.0]hexan-3-yl)methyl)-cyclopropyl)methanol, which may be combined in the range from 0.05:99.95 to 99.95:0.05 (e.g. in the range from 0.1:99.5 to 5:95 (including 0.2:99.8; 0.3:99.7, 0.4:99.6).

In another particular embodiment the compound of formula (I) is (1-methyl-2-(1S,3R,5R)-((1,2,2-trimethylbicyclo[3.1.0]hexan-3-yl)methyl)cyclopropyl)methyl acetate and the other woody odorant is (1-methyl-2-(((1S,3R,5R)-1,2,2-trimethylbicyclo[3.1.0]hexan-3-yl)methyl)-cyclopropyl) methanol, which may be combined in the range from 0.05: 99.95 to 99.95:0.05 (e.g. in the range from 0.1:99.5 to 5:95 (including 0.2:99.8; 0.3:99.7, 0.4:99.6; 0.5:99.5; 0.6:99.4, 0.7:99.3, 0.8:99.2, 0.9:99.1, 1:99, 1.5:98.5).

The compounds of formula (I) may be prepared by acetylation of the respective alcohol under conditions well known to the skilled person. The preparation of the respective alcohols is, e.g., described in EP 0 801 049.

Optionally, compounds of formula (I) wherein $R^1$ and $R^2$ form together with the carbon atom to which they are attached cyclopropyl and/or $R^3$ and $R^4$ form together with the carbon atom to which they are attached cyclopropyl, both, cyclopropanation and acetylation may be carried out together in a single pot process in the presence of zinc and, e.g., acetyl chloride. The ratio of alcohol to acetate being controlled by the amount of reagents used and by the appropriate selection of the distilled fractions of the crude product.

The invention is now further described with reference to the following non-limiting examples. These examples are for the purpose of illustration only and it is understood that variations and modifications can be made by one skilled in the art.

EXAMPLE 1: (1-METHYL-2-(((1S,3R,5R)-1,2,2-TRIMETHYLBICYCLO[3.1.0]HEXAN-3-yl) methyl)cyclopropyl)methyl Acetate To a reactor with a reflux condenser was charged under nitrogen 1-methyl-2-[[(1S,3R,5R)-1,2,2-trimethylbicyclo[3.1.0]hex-3-yl]methyl]cyclopropanemethanol) (mixture of diasteriomers; isomer 1: 40.9%; isomer 2: 53.4%; 50 g; purity: 94.3%; 212 mmol), pyridine (20 g; 253 mmol), and toluene (200 g). To the mixture stirred at 0° C., acetyl chloride (18 g; 229 mmol) were added dropwise within 15 minutes. The resultant reaction mixture was allowed to rise up to 20° C. and stirred for additional 2 hours. Water was added. The organic layer was separated, washed (water) and concentrated by rotavapory distillation (60° C.; 10 mbar) to give 58 g of a yellowish oil containing 90% of (1-methyl-2-(((1S,3R,5R)-1,2,2-trimethylbicyclo[3.1.0]hexan-3-yl)methyl)cyclopropyl)-methylacetate. Further purification by distillation using a 15 cm Vigreux column under 0.08 Torr afforded 48 g (purity: 93.9%; isomer 1: 41.4%; isomer 2: 52.5%; 170 mmol) of (1-methyl-2-(((1S,3R,5R)-1,2,2-trimethylbicyclo[3.1.0]hexan-3-yl)methyl)cyclopropyl)-methylacetate. More product could be recovered from 8.7 g of rejected (82% pure) fractions. (1-methyl-2-(((1S,3R,5R)-1, 2,2-trimethylbicyclo[3.1.0]hexan-3-yl)methyl)-cyclopropyl)methylacetate molar yield based on (1-methyl-2-(1,2,2-trimethylbicyclo(3.1.0)-hex-3-ylmethyl)cyclopropyl) methanol represented about 80% without taking into account rejected fractions. The 48 g obtained after the second distillation were further distilled using a Sulzer column (20 cm) leading to 40 g of 98% (isomer 1: 43.2%; isomer 2: 54.8%) of olfactory pure product ((1-methyl-2-(((1S,3R,5R)-1,2,2-trimethylbicyclo[3.1.0]hexan-3-yl)methyl)cyclopropyl)methylacetate).

Odor description: soft, woody creamy sandalwood character with a soft fruity floral aspect (violet/orris direction).

Isomer 1 (rel-(1R, 2R)-(1-methyl-2-(((1S,3R,5R)-1,2,2-trimethylbicyclo[3.1.0]hexan-3-yl)methyl)cyclopropyl)methyl acetate): $^1$H NMR ($C_6D_6$, 600 MHz): 3.83 (d, J=11.3, 1H), 3.77 (d, J=10.9, 1H), 1.95 (dd, J=12.4, 6.4, 1H), 1.73 (s, 3H), 1.37 (td, J=11.7, 4.1, 1H), 1.22-1.16 (m, 2H), 1.04 (s, 3H), 1.03 (s, 3H), 1.01-0.93 (m, 2H), 0.92 (s, 3H), 0.74 (s, 3H), 0.55-0.47 (m, 3H), 0.08 (dd, J=7.5, 4.5, 1H), −0.13 (br t, J=4.5, 1H). $^{13}$C NMR ($C_6D_6$, 150 MHz): 170.0, 73.2, 45.1, 41.1, 32.4, 31.2, 29.5, 22.8, 22.75, 21.4, 20.3, 19.5, 18.7, 17.4, 17.3, 15.3, 14.0

Isomer 2 (rel-(1S, 2S)-(1-methyl-2-(((1S,3R,5R)-1,2,2-trimethylbicyclo[3.1.0]hexan-3-yl)methyl)cyclopropyl)methyl acetate): $^1$H NMR ($C_6D_6$, 600 MHz): 3.84 (d, J=11.3, 1H), 3.79 (d, J=10.9, 1H), 1.88 (dd, J=12.1, 6.8, 1H), 1.72 (s, 3H), 1.37 (td, J=11.7, 4.1, 1H), 1.22-1.13 (m, 2H), 1.09-1.06 (m, 1H), 1.04 (s, 3H), 1.04 (s, 3H), 1.00-0.97 (m, 1H), 0.93 (s, 3H), 0.74 (s, 3H), 0.54-0.47 (m, 3H), 0.06 (dd, J=7.9, 4.9, 1H), −0.18 (br t, J=4.5, 1H).

$^{13}$C NMR ($C_6D_6$, 150 MHz): 170.0, 73.2, 44.8, 41.1, 32.2, 31.3, 28.8, 22.8, 22.6, 21.9, 20.2, 19.6, 19.6, 17.2, 16.8, 15.9, 13.9

EXAMPLE 2: WOODY, ORIENTAL FRAGRANCE ACCORD

| Compound/Ingredient | parts by weight 1/1000 |
| --- | --- |
| AMBRINOL (2,5,5-trimethyl-1,2,3,4,4a,5,6,7-octahydronaphthalen-2-ol) | 3 |
| ARMOISE essential oil | 2 |
| BOISIRIS (2-ethoxy-9-methylen-2,6,6-trimethylbicyclo[3.3.1]-nonane) | 50 |
| CASHMERAN (6,7-DIHYDRO-1,1,2,3,3-PENTAMETHYL-4(5H)-INDANONE) | 15 |
| CEDARWOOD essential oil | 10 |
| BUTANOIC ACID, 1,1-DIMETHYL-2-PHENYLETHYL ESTER | 4 |
| ETHYL LINALYL ACETATE (3,7-DIMETHYL-1,6-NONADIEN-3-YL ACETATE) | 10 |
| ETHYL MALTOL (3-HYDROXY-2-ETHYL-4H-PYRAN-4-ONE) | 1 |
| GALAXOLIDE (1,3,4,6,7,8-HEXAHYDRO-4,6,6,7,8,8-HEXAMETHYLINDENO(5,6-C)PYRAN) | 80 |
| GARDENOL (1-PHENYLETHYL ACETATE) | 1 |
| HEDIONE (methyl 3-oxo-2-pentylcyclopentaneacetate) | 40 |
| IONONE BETA (4-(2,6,6-TRIMETHYL-1-CYCLOHEXEN-1-YL)-3-BUTEN-2-ONE) | 10 |
| ISO E SUPER | 430 |
| ISORALDEINE | 8 |
| LEMON OIL | 6 |
| CIS-3-HEXENYL METHYL CARBONATE | 3 |
| LINALOOL | 7 |
| MAHONIAL (9-HYDROXY-5,9-DIMETHYLDEC-4-ENAL) | 10 |
| NYMPHEAL (3-(4-isobutyl-2-methylphenyl)propanal) | 5 |

-continued

| Compound/Ingredient | parts by weight 1/1000 |
| --- | --- |
| PATCHOULI OIL | 4 |
| ROSYFOLIA ((1-methyl-2-(5-methylhex-4-en-2-yl)cyclopropyl)methanol) | 4 |
| VANILLIN (4-HYDROXY-3-METHOXYBENZALDEHYDE) | 5 |
| VETIVER OIL | 2 |
| DIPROPYLENE GLYCOL | 290 |
| Total: | 1000 |

The replacement of 4 parts of DPG of the accord above by (1-methyl-2-((1,2,2-trimethylbicyclo[3.1.0]hexan-3-yl)methyl)cyclopropyl)-methyl acetate (i.e. a compound of formula (I)) softens the accord both, on fresh and dry down, and brings in particular a soft creamy orris violet to the dry down note.

The replacement of 20 parts of DPG of the accord above by a mixture of (1-methyl-2-((1,2,2-trimethylbicyclo[3.1.0]hexan-3-yl)methyl)cyclopropyl)-methyl acetate and (1-methyl-2-((1,2,2-trimethylbicyclo[3.1.0]hexan-3-yl)methyl)cyclopropyl)-methanol (in a ratio of 2:98), alcohol delivers performance and the overall sandalwood character, soften by the combination with the acetate, with a general sandalwood character which appears more natural, closer to the sandalwood essential oil effect and character, with the soft fruity floral orris facet.

The invention claimed is:

1. A compound of formula (I) in the form of any one of its stereoisomers or a mixture thereof

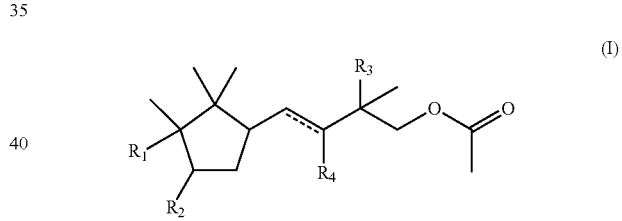

wherein
$R^1$ and $R^2$ form together with the carbon atoms to which they are attached cyclopropyl or a double bond, or $R^1$ and $R^2$ are hydrogen; and
$R^3$ and $R^4$ form together with the carbon atom to which they are attached cyclopropyl, and the dotted line together with the carbon-carbon bond forms a single bond; or
$R^3$ and $R^4$ are hydrogen, and the dotted line together with the carbon-carbon bond forms a double bond, wherein $R^1$ and $R^2$ and $R^3$ and $R^4$ form together with the carbon atom to which they are attached cyclopropyl, and wherein the compound is (1-methyl-2-((1,2,2-trimethylbicyclo[3.1.0]hexan-3-yl)methyl)cyclopropyl)-methyl acetate in the form of any one of its stereoisomers or a mixture thereof.

2. The compound according to claim 1, wherein the compound is (1-methyl-2-(((1S,3R,5R)-1,2,2-trimethylbicyclo[3.1.0]hexan-3-yl)methyl)cyclopropyl)-methyl acetate.

3. A fragrance composition comprising:
a) at least one compound of formula (I) as defined in claim 1, and b) [1-methyl-2-[(1,2,2-trimethylbicyclo[3.1.0]hex-3-yl)methyl]cyclopropyl]methanol in the form of any one of its stereoisomers or a mixture thereof.

4. The fragrance composition according to claim 3, wherein the compound of formula (I) is (1-methyl-2-(((1S,3R,5R)-1,2,2-trimethylbicyclo[3.1.0]hexan-3-yl)methyl)cyclopropyl)-methyl acetate), and b) is [1-methyl-2-[((1S,3R,5R)-1,2,2-trimethylbicyclo[3.1.0]hex-3-yl)methyl]cyclopropyl]methanol.

5. The fragrance composition according to claim 3 wherein the weight ratio of a) to b) is in the range from 0.05:99.95 to 5:95 (a:b).

6. A consumer product comprising a compound of formula (I) as defined in claim 1 and a consumer product base.

7. A method comprising utilizing a compound of formula (I) as a fragrance

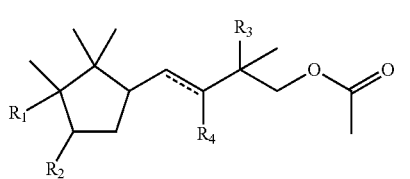

wherein
$R^1$ and $R^2$ form together with the carbon atoms to which they are attached cyclopropyl or a double bond, or $R^1$ and $R^2$ are hydrogen; and
$R^3$ and $R^4$ form together with the carbon atom to which they are attached cyclopropyl, and the dotted line together with the carbon-carbon bond forms a single bond; or
$R^3$ and $R^4$ are hydrogen, and one of the dotted line together with the carbon-carbon bond forms a double bond; wherein $R^1$ and $R^2$ and $R^3$ and $R^4$ form together with the carbon atom to which they are attached cyclopropyl, and wherein the compound is (1-methyl-2-((1,2,2-trimethylbicyclo[3.1.0]hexan-3-yl)methyl) cyclopropyl)-methyl acetate in the form of any one of its stereoisomers or a mixture thereof, the method comprising mixing the compound of formula (I) with a consumer product base, or mixing a fragrance composition comprising the compound of formula (I) with a consumer product base.

8. A method of improving, enhancing or modifying a consumer product base by adding thereto an olfactory acceptable amount of a compound of formula (I) as defined in claim 7.

9. A fragrance composition consisting of:
a) at least one compound of formula (I) as defined in claim 7, and
b) [1-methyl-2-[(1,2,2-trimethylbicyclo[3.1.0]hex-3-yl)methyl]cyclopropyl]methanol in the form of any one of its stereoisomers or a mixture thereof.

10. A fragrance composition consisting of:
a) at least one compound of formula (I) as defined in claim 1, and
b) [1-methyl-2-[(1,2,2-trimethylbicyclo[3.1.0]hex-3-yl)methyl]cyclopropyl]methanol in the form of any one of its stereoisomers or a mixture thereof.

11. The fragrance composition according to claim 4 wherein the weight ratio of a) to b) is in the range from 0.05:99.95 to 5:95 (a:b).

12. A consumer product comprising a fragrance composition as defined in claim 3 and a consumer product base.

13. A consumer product comprising a fragrance composition as defined in claim 4 and a consumer product base.

14. A consumer product comprising a fragrance composition as defined in claim 5 and a consumer product base.

15. A method of improving, enhancing or modifying a consumer product base by adding thereto an olfactory acceptable amount of a fragrance composition as defined in claim 2.

16. A method of improving, enhancing or modifying a consumer product base by adding thereto an olfactory acceptable amount of a fragrance composition as defined in claim 3.

* * * * *